United States Patent [19]

Gallop et al.

[11] Patent Number: 4,713,346
[45] Date of Patent: Dec. 15, 1987

[54] FORMATION OF ANALYZABLE BORON CONTAINING ADDUCTS

[75] Inventors: Paul M. Gallop; Edward Henson, both of Chestnut Hill, Mass.; Rudolf Flückiger, Basel, Switzerland

[73] Assignee: The Children's Medical Center Corporation, Boston, Mass.

[21] Appl. No.: 825,619

[22] Filed: Feb. 3, 1986

[51] Int. Cl.$^4$ .................. G01N 24/00; G01N 30/00; G01N 33/00
[52] U.S. Cl. ........................... 436/86; 436/89; 436/90; 436/92; 436/93; 436/98; 436/111; 436/128; 436/129; 436/131; 436/161; 436/162; 436/164; 436/173; 436/182
[58] Field of Search ............ 436/86, 89, 90, 91, 436/92, 96, 97, 98, 129, 131, 161, 162, 106, 111, 164, 173, 182, 183, 128, 93

[56] References Cited

FOREIGN PATENT DOCUMENTS 0200485  5/1983  Fed. Rep. of Germany ...... 436/161
0072054  4/1983  Japan .................................. 436/161

OTHER PUBLICATIONS

Megges et al, Chemical Abstracts, vol. 89, Abstract No. 159644x, 1978.
Gordon, Journal of the A.O.A.C., vol. 45, No. 3, pp. 785–786, 1962.
Nefkens et al., (1983), Tetrahedron 39:2295.
Fluckiger et al., (1984), Biomedical Mass Spectrometry 11:611.

Primary Examiner—Barry S. Richman
Assistant Examiner—Robert J. Hill, Jr.

[57] ABSTRACT

A method of forming analyzable adducts in a mixture of compounds by contacting the mixture with a boron reagent having the formula of either

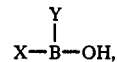

where each X and Y is, independently, an alkyl group of 12 or fewer carbons or an aryl group of 6–20 carbons; or $BZ_3$, where each Z is, independently, an alkyl group of 12 or fewer carbons, or an aryl group of 6–20 carbons.

29 Claims, 2 Drawing Figures

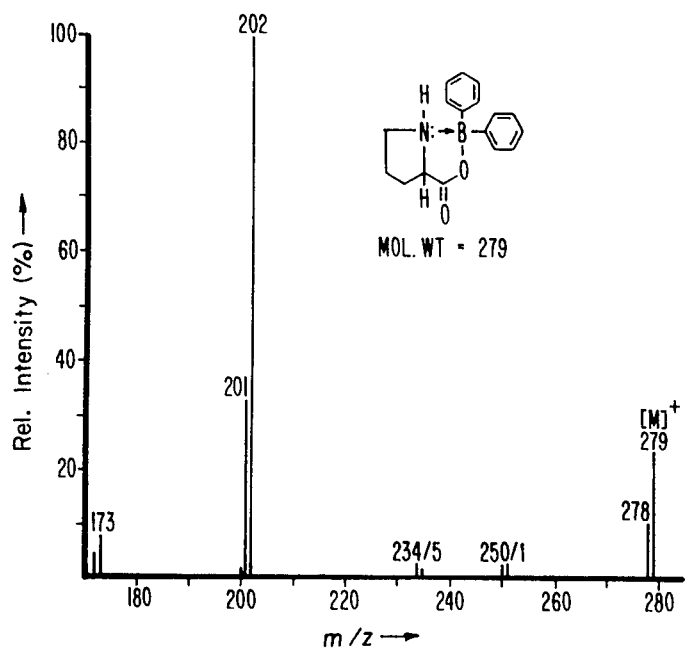
FIG 1 70 eV electron impact mass spectrum of the diphenylborinate complex of proline.
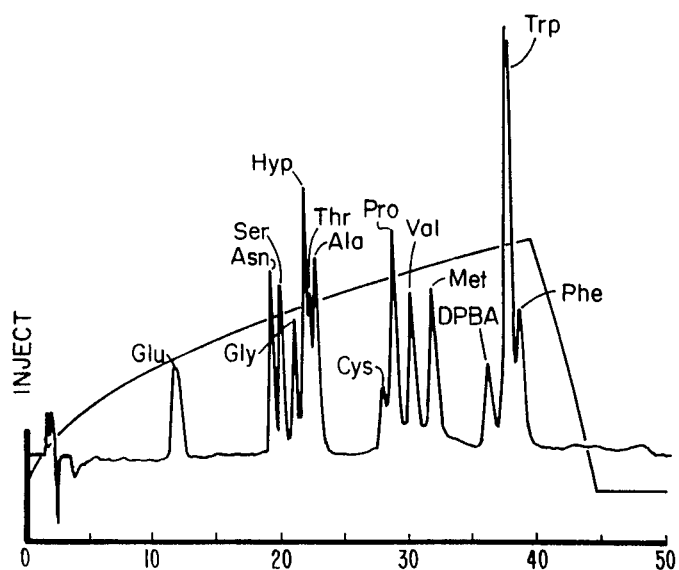
FIG 2 Separation of 13 diphenylborinate amino acid adducts by HPLC on uBondapack C-18.

FORMATION OF ANALYZABLE BORON CONTAINING ADDUCTS

BACKGROUND OF THE INVENTION

This invention relates to the analysis of organic compounds.

A mixture of amino acids is typically separated into its components by ion exchange chromatography. The amino acids eluted can be detected and quantified using the standard ninhydrin reaction; the amino acids are not recoverable after this reaction.

Nefkens et al., 39 Tetrahedron 2995 (1983), discloses that α-amino acids react with diaryl or dialkylborinic acids to yield 1,1-diaryl or dialkylboroxazolidones having the structure

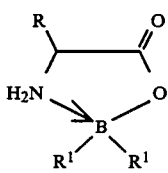

SUMMARY OF THE INVENTION

In general, the invention features a method of forming analyzable adducts in a mixture of organic compounds by contacting the mixture with a boron reagent having the formula $$X-\overset{Y}{\underset{|}{B}}-OH,$$

where each X and Y is, independently, an alkyl group of 12 or fewer carbons or an aryl group of 6–20 carbons; or $BZ_3$, where each Z is an alkyl group of 12 or fewer carbons, or an aryl group of 6–20 carbons.

Most preferably, in the boron reagents each X, Y, and Z is an aryl group of 6–12 carbons to provide good UV absorption for detection of the adducts. Preferred reagents of the invention include 1,1-diphenylborinic acid and triphenylboron.

The compounds in the mixture which form the analyzable adduct preferably contain the functionality

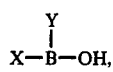

where —OH is either a hydroxy or the —OH portion of a carboxyl group, and N is part of an amino group, an imino group, or an aromatic heterocycle. Preferably, the analysis is performed by either high performance liquid chromatography, wherein the adducts are detected by UV absorption, their retention times are compared to those of known controls, and the quantity of each adduct is determined; thin layer chromatography, wherein the adducts are detected by UV absorption and the $R_f$'s of the adducts are compared to those of known controls; or mass spectroscopy, wherein during the analysis the adducts are detected by UV absorption and the mass spectra of the adducts are compared to the mass spectra of known controls.

In other preferred embodiments, the mixture is a protein hydrolysate; a mixture of different α-amino acids; a mixture of different 2-carboxypyrazines; or a mixture of different γ-glutamyl peptides.

In other preferred embodiments, the mixture contains primary or secondary alcohols or primary or secondary amines and, prior to contacting the mixture with the boron reagent, the mixture is contacted with a compound having the functionality of either

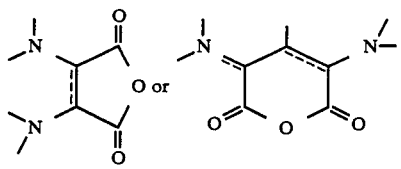

where N is part of an amino group, an imino group, or an aromatic heterocycle, to form a compound containing the reactive functionality

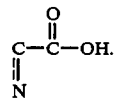

Particular alcohols that can be analyzed include the steroidal alcohols.

In other preferred embodiments, the mixture contains a ketone or aldehyde and, prior to contacting the mixture with the boron reagent, the mixture is contacted with a compound that, in addition to having the

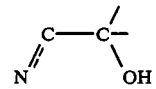

functionality discussed above, also contains a hydrazide group, to form a compound that contains both the

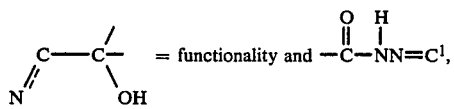

where $C^1$ is the carbonyl carbon from the aldehyde or ketone. Particular preferred hydrazine-containing compounds include amino acids, such as γ-glutamyl hydrazide and β-aspartyl hydrazide, and nitrogen-containing aromatic heterocycles, for example,

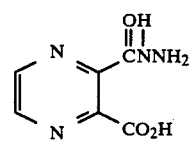

In other preferred embodiments, the mixture contains a primary amine and, prior to contacting the mixture with the boron reagent, the mixture is contacted with either an α-ketoacid or glyoxylic acid, and $NaCNBH_4$, to form an α-amino acid in which the α-amino group is a secondary amino group.

The invention also features a method of forming analyzable adducts of α-amino acids present in a mixture by reacting the mixture with the adduct produced by the reaction of an α-amino alcohol with the boron reagents described above. An example of such an α-amino alcohol adduct is the ethanolamine:1,1-diphenylborinic acid adduct. The analyzable adducts are analyzable by high pressure liquid chromatogrpahy, thin layer chromatography, or mass spectroscopy.

The methods of the invention provide useful methods for analyzing a sample for certain types of compounds (e.g., α-amino acids). The boron reagents react well with the compounds to form stable adducts that lend themselves to analysis. The adducts can be readily resolved by various chromatographic techniques and the starting compounds can be recovered after separation.

Particularly useful is that the adducts formed by the method of the invention can be easily detected. In addition to conventional detection techniques (e.g., the ninhydrin reaction for α-amino acid adducts), the boron reagent can be selected so that it contains groups that exhibit good UV absorption, i.e., groups that are readily detected by conventional UV techniques, including UV spectroscopy and UV detection on thin layer chromatography plates. With respect to α-amino acids, most of which do not exhibit good UV absorption, conversion to adducts that have good UV absorption facilitates detection. The detection limits of the methods of the invention, which are approximately 1 nanomole, can be further improved by selecting boron reagents that have attached fluorescent groups, by employing boron absorption spectroscopy, or by neutron activation of boron to yield detectable α-particles.

The adducts formed by the methods of the invention are conveniently analyzable by mass spectroscopy. Many biologically important molecules, such as amino acids, are nonvolatile and thus not readily susceptible to mass spectrographic studies. By reacting there molecules with the reagents of the invention, adducts are produced which are sufficiently volatile for such studies. In addition, the adducts formed are readily analyzable because compounds that contain boron can be easily identified by the signals caused by the 4:1 loss of $B^{11}$:$B^{10}$ isotopes.

Other features and advantages of the invention will be apparent from the following description of the preferred embodiments thereof, and from the claims.

DESCRIPTION OF THE PREFERRED EMBODIMENT

The drawings will be described first.

BRIEF DESCRIPTION OF THE DRAWINGS

FIG. 1 is a mass spectrum of the diphenylborinate adduct of proline.

FIG. 2 displays the separation of 13 diphenylborinate amino acid adducts by high pressure liquid chromatography.

BORON REAGENTS

The boron reagents of this invention preferably have the formula

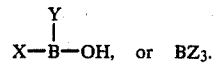

(1)    (2)

The reagents having formula (1) are disubstituted borinic acid derivatives. Each X and Y can be, independently, a substituted (e.g., with halogen) alkyl group of 12 or fewer carbons, more preferably fewer than 5 carbons, or a substituted (e.g., with halogen or an alkyl group) aryl group of 6-20 carbons, more preferably 6-12 carbons. Diethylborinic acid is an example of a dialkylborinic acid reagent. Preferably, both X and Y are aryl groups that provide good UV absorption or fluorescence, to allow for easy detection of derivatives formed from the reagents. Examples of diarylborinic acids with good UV absorption are diphenylborinic acid (DPBA) and ditolylborinic acid. Dinapthylborinic acid is an example of a diarylborinic acid exhibiting good fluorescence.

Reagents having structure (2) are trisubstituted boron derivatives. Each Z, independently, can be a substituted (e.g., halogen) alkyl group of 12 or fewer carbons, more preferably fewer than 5 carbons, or a substituted (e.g., halogen or an alkyl group) aryl group of 6-20 carbons, more preferably 6-12 carbons. Preferably Z is an aryl group providing good UV absorption or fluorescence; triphenylboron (TPB) is an example of a triarylboron with good UV absorption. Reagents having structure (2) can be generated in situ from tetrasubstituted boron salts having the structure $$WBZ_3,$$

(3)

wherein W is a cation capable of forming a salt with the tetrasubstituted boron anion. Compounds having structure (3) form the trisubstituted boron derivatives when exposed to aqueous acid.

Boron reagents of both structure (1) and (2) can be used to form the derivatives discussed below. With substrates containing a tertiary amine, however, use of reagents having structure (1) is preferred, since reagents having structure (2) react slowly with these substrates because of steric hindrance resulting from the presence of the third alkyl or aryl group.

Reaction of Boron Reagents with Substrates

In the following discussion, DPBA and TPB are used as representative of the boron reagents.

The boron reagents can be reacted with substrates that contain functionality (4) to form derivatives that can be readily analyzed.

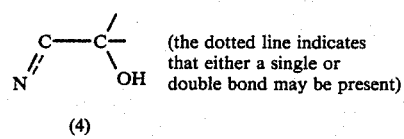 (the dotted line indicates that either a single or double bond may be present)

(4)

In (4), the —OH can be an alcohol or the —OH portion of a carboxyl group; the N can be a part of an amino group, an imino group, or an aromatic heterocyclic ring. A substrate containing functionality (4) reacts with DPBA or TPB to form a derivative (adduct) having structure (5), wherein the B—N bond is a coordination bond and the B—O bond is a covalent bond.

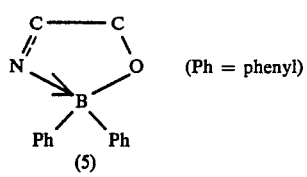

(Ph = phenyl)

One class of compounds that have functionality (4) are the α-amino acids, which react with either DPBA or TPB to form 1,1-diphenylboroxazolidones. Scheme 1 sets forth the general reaction.

Scheme 1

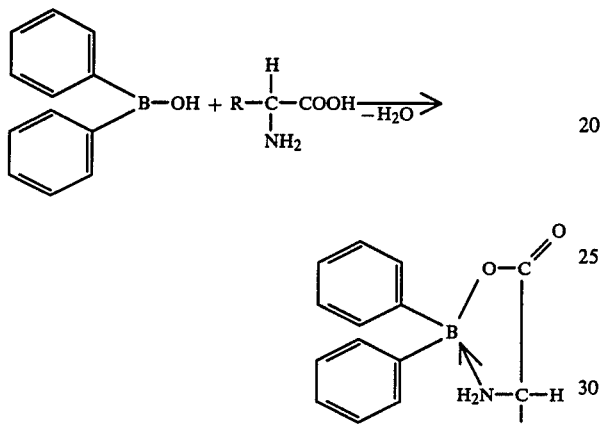

The reaction between α-amino acids and DPBA is usually carried out in ethanol-water under slightly acidic pH with a slight excess of the reagent. The reaction also proceeds well with TPB, although generally the solution must be heated. TPB can be generated in situ; a particularly simple way to run the reaction is to use amino acid hydrochlorides (as found in acid hydrolysates of proteins with the excess acid removed by several evaporations in vacuo) and excess sodium tetraphenylboron. In this manner, TPB is generated in just the amount needed to react with the neutralized amino acid generated by the base released by the acidic decomposition of the sodium tetraphenylboron.

The 1,1-diphenylboroxazolidones that are formed are quite resistant to hydrolysis. They can be heated for prolonged periods in aqueous buffers from pH 2–5 without significant hydrolysis. At pH<2, the compounds hydrolyze to give the α-amino acid and DPBA.

α-Amino alcohols react with DPBA or TPB to form 1,1-diphenylboroxazolidines (scheme 2).

Scheme 2

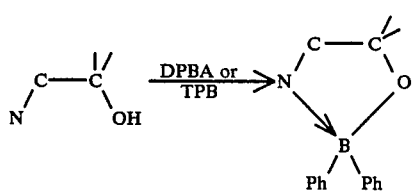

These compounds are stable under neutral conditions but are acid labile. This property allows these compounds to undergo a type of transborination when reacted with an amino acid hydrocholoride; the more stable 1,1-diphenylboroxazolidone is formed along with the amino alcohol hydrochloride byproduct (scheme 3)

Scheme 3

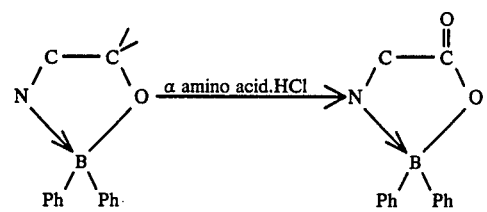

The commercially available ethanolamine adduct of DPBA can thus be used to produce 1,1-diphenylborazolidones. The reaction can also be run with α-amino acids in dilute acetic acid; under these conditions, DPBA is generated in situ with formation of the acetate salt of ethanolamine as a side product.

Alcohols, amines, and carbonyl compounds can be converted into functionality (4)-containing substrates that can be reacted with the boron reagents of the invention. Anhydrides containing functionality (6) or (7), where each N is a portion an amino group, an imino group, or an aromatic heterocycle, can be reacted with primary and secondary alcohols

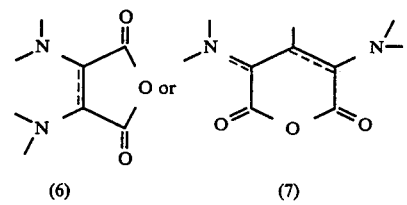

and amines to form derivatives that have a 2-carboxylic acid adjacent to the nitrogen atom. These derivatives can then be reacted with DPBA to yield adducts that can be analyzed by the methods of the invention. For example, 2,3-pyrazinedicarboxylic acid anhydride can be reacted with primary and secondary alcohols or primary and secondary amines to form 3-carboxyesters or 3-carboxyamides amides. Addition of DPBA to these compounds in water leads to the formation of an adduct in which a 1,1-diphenyldehydro-boroxazolidone is fused to the 1,2 positions of the pyrazine (scheme 4). Amines of biological interest much as dopamine and serotonin, and alcohols such as the steroidal alcohols, e.g., estradiol, can be converted by these methods into derivatives that can be readily analyzed.

Scheme 4

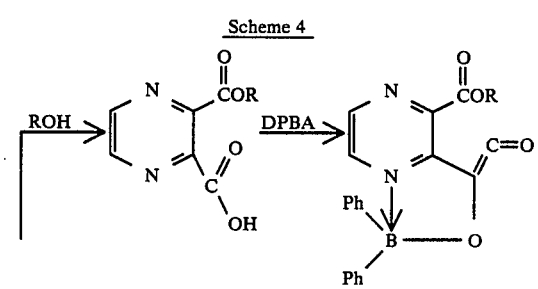

-continued
Scheme 4

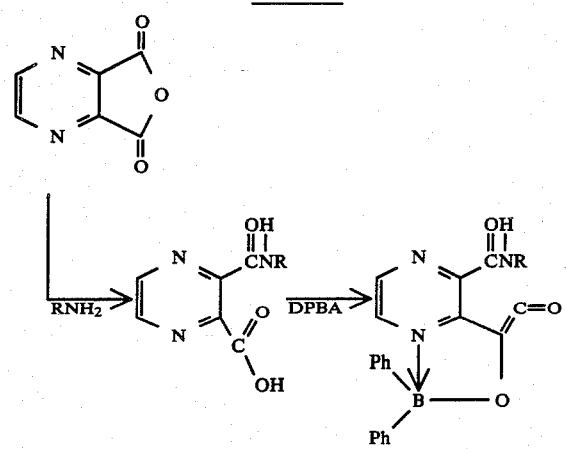

A slight variation of the above procedure, for use with amines, involves heating an amine hydrochloride with 2,3-pyrazinedicarboxylic acid anhydride and sodium tetraphenylboron. The base produced from the decomposition of sodium tetraphenylboron promotes the release of the free amine and its acylation by the anhydride. This generates the borinate binding site for the 1,1-diphenylborinate that arises from the previously generated TPB and results in the formation of the 5-membered heterocyclic adduct.

Compound (8) is an example of a functionality (7)-containing molecule.

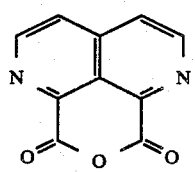

(8)

Various carboxyl compounds, for example, ketones such as acetone, aldehydes such as acetylacetone, and ketoacids such as pyruvic acid, can be reacted with substrates containing functionality (4) that also contain a hydrazide

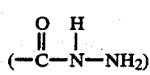

to form a derivative that can be reacted with the boron reagents of this invention. For example, in scheme 5, α-carboxypyrazine-3-carboxyhydrazide (9) is reacted with a Scheme 5

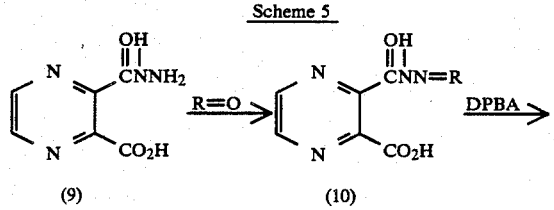

-continued
Scheme 5

carbonyl compound, such as acetone, acetylacetone, or pyruvic acid, to give derivative (10), which is then reacted with DPBA to yield analyzable adduct (11). Hydrazide containing amino acids such as γ-qlutamyl hydrazide and β-aspartyl hydrazide can also be used as the substrate.

Primary amines can be reductively carboxylated with α-ketoacids (11a) or glyoxylic acid and NaCNBH$_3$ to form an α-amino acid (11b), which can then be reacted with DPBA or TPB to produce a boron adduct (11c) (scheme 6) that can be readily analyzed.

Scheme 6

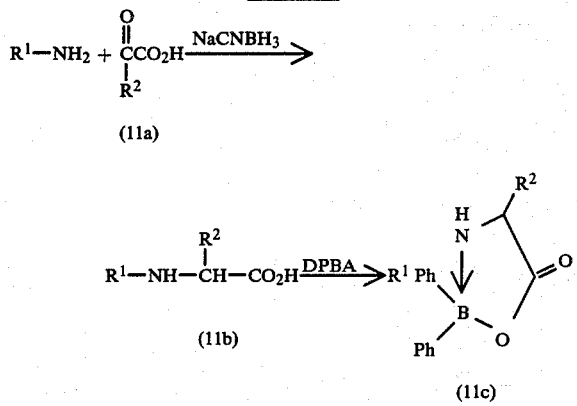

Analysis of Boron Adducts

The adducts of the invention are readily separated from each other and from DPBA and its major decomposition products, phenol and phenylboronic acid, by both high performance liquid chromatography (HPLC) and thin layer chromatography (tlc). Detection of the adducts using either technique can be by UV absorption, fluorescence (in some cases), and by various reagents. For example, 1,1-diphenylboroxazolidones can be detected by the standard ninhydrin reaction, which causes decomposition of the boroxazolidones to their constituent amino acids; and fluorimetrically with phthalaldehyde, where the alkaline conditions used cause the decomposition of the boroxazolidones. In addition, 2-carboxypyrazine compounds, such as those in schemes 4 and 5, can be detected by their ability to chelate iron and give a reddish pink color. The detection limit of this methodology, which is approximately one nanomole, may be increased considerably either by employing fluorescent 1,1-diarylborinic acids, by the use of boron atomic absorption spectroscopy, or by making use of the reacton of boron with slow neturons to release easily detectable α-particles.

Adducts (5) can also be analyzed by mass spectroscopy. Many biologically important molecules are non-volatile and thus not readily susceptible to mass spectrographic studies. By reacting these molecules with the reagents of the invention, derivatives are produced which are sufficiently volatile for such studies.

Mass spectroscopy is a particularly useful method of analyzing compounds containing boron in that the ion signal originating from boron containing compounds can be easily identified because of the signals caused by the 4:1 ratio of $B^{11}:B^{10}$ isotopes. Also, diphenylboroxazolidones, for example α-amino acid:DPBA aducts, exhibit all the losses typically observed for the boroxazolidone ring, i.e. (a) the elimination of a phenyl group $[M-77]^+$ by radical loss from the parent ion, giving rise to an ion signal which is often the base peak, (b) a neutral benzene elimination $[M-78]^{+\cdot}$, (c) the loss of carbon monoxide $[M-28]^+$ and carbon dioxide $[M-44]^+$ from either $[M]^{+\cdot}$ or $[M-1]^+$ by ring contraction, and (d) a combination thereof $[M-78-28]^+$. The 77/78 fragmentation pattern is consistent with the transition of the tetragonal conformation of the boron to the triagonal state. In this process, a phenyl group is eliminated which tends to combine with a proton and result in a neutral benzene loss. The fragmentation process leading to the formation of the covalent B—N bond yields an odd electron ion which is equivalent to that which can be obtained directly by reaction of the boronic acid with an amino acid. The resulting planar molecule with the triagonal boron should show little tendency to fragment further. Such an adduct ion can be observed from the reaction in low yield of phenylboronic acid with amino acids under similar reaction conditions. The ions observed from these products only exhibited side-chain losses (scheme 7).

Scheme 7. Mode of fragmentation of the state of the stable diphenylboronate (1) and labile phenylboronate (2) amino acid adducts.

The reactive properties of DPBA with compounds containing functionality (4) and the ability to readily analyze the adducts formed can be utilized in a variety of ways. For example, a sample containing amino acids, for example, a protein hydrolysate, can be reacted with excess DPBA and the resultant sample run through HPLC to separate the various components (using the detection techniques discussed above, e.g., UV absorption) and to identify them by comparing their retention times to control samples. The amount of each DPBA:α-amino acid adduct can be determined by measuring the area under the peak associated with a particular adduct. Tlc can also be employed, with the $R_f$'s of the derivatized components being compared with the known $R_f$'s of the controls. In addition, the mass spectrum of the reaction sample can be compared to control spectra, and the α-amino acid adducts present can be determined.

The methods of the invention can be used to analyze the γ-glutamyl peptides, for example glutathione, that may be present in a biological sample. Excess trichloroacetic acid (TCA) is added to a cell or tissue homogenate to precipitate proteins and nucleic acids; the γ-glutamyl peptides and any free amino acids remain in solution as TCA salts. Excess TCA is extracted with ether. Excess sodium tetraphenylboron is added and, with heating, the TPB generated derivatizes the γ-glutamyl peptides and the amino acids; many of adducts are now insoluble and extractable into non-polar solvents. Furthermore, γ-glutamyl peptides and α-amino acids having amino, guanidino, or imidazole groups on sidechains are generally water soluble at this stage, since they exist as cationic salts at mildly acidic pH.

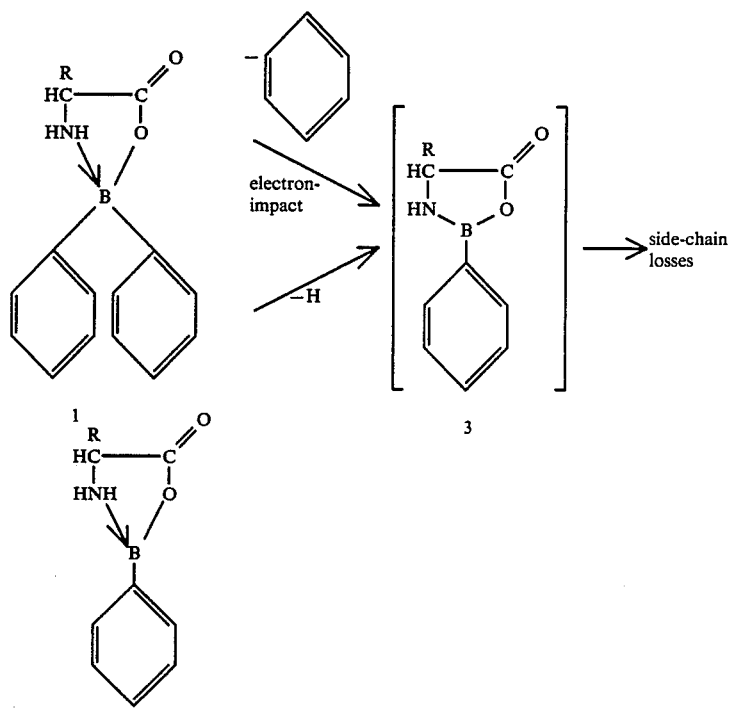

However, additional sodium tetraphenylboron can now be added to promote the precipitation of these compounds as insoluble cationic salt of the tetraphenylboron anion. The adducts isolated at either stage can be analyzed by the methods discussed above.

A mixture of peptides can be analyzed by the methods of this invention. The mixture can be contacted with 2,3-pyrazinedicarboxylic acid anhydride, which reacts with the ε-amino groups of the peptides to form 3-amide derivatives of 2-caboxypyrazine. These can then be reacted with DPBA and analyzed by the methods discussed above.

Hydroxylated steroids can also be analyzed by the methods of this invention. Lipid soluble steroids can be extracted from tissue by standard methods. The extracted material is first reacted with 2,3-pyrazinedicarboxylic acid anhydride to give the 3-ester steroid derivatives of 2-carboxypyrazine; these derivatives are then reacted with DPBA to give cyclic adducts that can be analyzed by the methods of the invention.

Specific Procedures

This section presents examples of specific procedures that can be utilized to obtain DPBA adducts. Useful analytical data are given for several α-amino acid:DPBA derivatives. The data can be used for comparision to that obtained when the procedures are carried out on samples containing unidentified substrates.

Reagents and Equipment

The ethanolamine complex of diphenylborinic acid was obtained from Aldrich Chemical Company (Milwaukee, Wis.). All other chemicals were commercial products of the highest available purity. Electron impact (EI) mass spectra in positive ion mode were obtained on a Hitachi RMU-6E mass spectrometer at 70 eV using a direct inlet. Samples were vaporized at 100°-170° C. High performance liquid chromatography was performed on a Waters instrument with a 5 Å μC18 Bondapack column (8 mm×10 cm). The DPBA complexes were eluted with gradient curve No. 5 starting from solvent A consisting of 5% THF in 5 mM sodium phosphate, pH 5.5, to 50% solvent B, acetonitrile. The flow rate was 2 ml min$^{-1}$ and the effluent was monitored at 268 nm with a Waters M-450 absorbance detector. Melting points were determined on a Fisher-Johnes melting point block. The elemental analysis was performed by Galbraith Labs, Knoxville, Tenn.

Preparation of DPBA

The DPBA ethanolamine complex was dissociated in 1M HCl (30 min under nitrogen) and the free DPBA extracted with methylene chloride. The methylene chloride was washed twice with water and once with brine, dried with sodium sulfate, and evaporated under reduced pressure. The oil was taken up in warm hexane, from which white crystals precipitated upon cooling. They were collected by filtration, washed and recrystallized from hexane (m.p. 128°-130° C.). Crystallization from benzene gave a melting point of 116°-128° C. in agreement with the value obtained by Coates et al., 1961 J. Chem. Soc. 4909. The mass spectrum of this pure DPBA showed ion signals at m/z 182([M]+·, 25%); 181 ([M-1+, 12%); 165 ([M-17]+, 100%); 105 ([M-77], 25%); 104 ([M-78]+, 10%) as well as for some of the anhydrides listed in table 1. (The ion signals of the anhydrides are useful for distinguishing unimportant signals in mass spectra of α-amino acid:DPBA adducts.) DPBA kept dry and under nitrogen only slowly oxidizes to a brownish material containing hydrolytic products such as phenol and phenylboronic acid. Freshly prepared DPBA can be used for up to three months.

TABLE 1

Mass sectral artifact peaks arising from reagent and breakdown products

| Formula | m/z | Designation |
|---|---|---|
| (Ph)$_2$B—OH | 182 | Diphenylborinic acid |
| (Ph)B—$_2$OCH$_2$CH$_2$NH$_2$ | 225 | Ethanolamine complex of DPBA |
| B(Ph)$_3$ | 242 | Putative triphenylboron |
| (PhBO)$_3$ | 312 | Trimeric boronic acid anhydride |
| (Ph)$_2$B—O—B(Ph)$_2$ | 346 | DPBA anhydride |
| (Ph)$_2$B—O—B(Ph)$_2$: NH$_2$CHCH$_2$ | 389 | Putative anhydride between the ethanolamine complex and DPBA after water loss |
| PhB(O—B(Ph)$_2$)$_2$ | 450 | Mixed boronic-boronic acid anhydride |

Derivatization Procedures for Amino Acids

1. Reaction of Amino Acids with DPBA (General Procedure)

Miligram quantities of the compounds of interest were reacted with an equimolar amount of DPBA, or the respective molar excess if other than 1:1 complexes could result. Derivatization was performed in ethanol:water (1:1). The solution was heated to 60°-70° C. for 15 minutes. Upon cooling of the reaction mixture, crystallization of the ethanolamine and amino acid adducts containing no polar functional groups in the side chain occurred. Reaction mixtures of compounds not yielding crystalline products were evaporated and the residues dissolved in an appropriate solvent such as ethanol or methanol and inserted directly into the mass spectrometer cup or into the HPLC apparatus. Certain of the crude products which did not crystallize immediately from the reaction mixture could be crystallized from water, water-ethanol, or methylene chloride. Melting points and mass spectra data for the derivatives are set forth in table 3. Elemental analysis of the DPBA complex of proline showed close agreement between the calculated (C, 73.15%; H, 6.49%; B, 3.87%; N, 5.02%) and experimental values (C, 72.83%; H, 6.61%; B, 4.05%; N, 5.01%).

2. Reaction of L-Alanine and TPB

To 100 ml of TPB solution (obtained from Dupont) in a nitrogen atmosphere are added 7.5 ml of concentrated HCl over two minutes followed by 17.5 ml of 7% HCl over 5 minutes. The mixture is stirred 5 minutes, filtered, washed with water, sucked dry under N$_2$, and stored in a dark bottle under N$_2$ until needed.

0.25 g TPB, 0.09 g L-alanine, 1 ml water, and 3 ml ethanol are mixed together and gently refluxed for 16 hours. The solvent was then removed under N$_2$ and the resultant solid product washed with water. 0.2 g of the product was obtained.

3. Reaction of L-Tyrosine and NaB(Ph)$_4$ 0.18 g L-tyrosine, 0.34 g NaB(Ph)$_4$, 0.1 ml concentrated HCl, and 60 ml water were mixed together and refluxed for 16 hours. 0.17 g of the solid product was filtered off while the solution was still hot. The product was further purified by washing with 5 ml benzene and 5 ml cyclohexane.

2 summarizes the mass spectra of other amino acid:D-PBA complexes.

TABLE 2

Characterization of L-amino acid:DPBA complexes

| Amino acid | Adduct ratio | Base peak ratio [M]+·(1:1)/[M]+·(1:2) | m.p.[b] | Main losses from boroxazolidone ring intensity of respective ion signal[a] | | | Additional losses loss, (intensity) |
|---|---|---|---|---|---|---|---|
| | | | | [M]+·(m/z) | [M]+·/[M-1]+ | [M-77]+/[M-78]+ | |
| Gly | 1:1 | | 253–254 | 239 | 65/13 | 100/83 | |
| Ala | 1:1 | | 240–243 | 253 | 52/16 | 100/30 | |
| Val | 1:1 | | | 281 | 56/27 | 100/42 | 120(65) |
| Leu | 1:1 | | | 295 | 39/14 | 100/30 | 85(13) |
| Phe | 1:1 | | 242–243 | 329 | 36/16 | 100/91 | 92(11), 119(15), 105(8) |
| Pro | 1:1 | | 300d | 279 | 24/11 | 100/33 | 106(8) |
| Met | 1:1 | | 232–235 | 313 | 29/7 | 82/78 | 105(100) |
| Ser | 1:1 | 0.028 | 212–215d | 269 | 100/42 | 69/56 | 18(24), 47(14), 95(28) |
| | 1:2 | | | 433 | 20/10 | 20/16 | 155(100) |
| Thr | 1:1 | 12.5 | 199–200d | 283 | 100/35 | 92/84 | 18(2), 95(16) |
| | 1:2 | | | 447 | 39/16 | 39/22 | 155(100) |
| Tyr | 1:1 | 12.5 | | 345 | 19/5 | 29/100 | |
| | 1:2 | | | 509 | 1/0.5 | 4/8 | 121(2), 155(1), 238(100) |
| Hyp | 1:1 | 0.02 | 273–278 | 295 | 22/11 | 100/38 | 95(19) |
| | 1:2 | | | 459 | 34/27 | 100/60 | 106(8) |
| Cys | 1:1 | | 228–229 | 285 | 100/31 | 72/36 | 34(38) |
| Glu | 1:1 | | | 311 | 35/10 | 27/83 | 96(100), 97(28) |
| Asp | 1:1 | | >300 | 297 | 11/4 | 31/100 | 62(31) |
| Lys | 1:1 | 0.03 | 263–264d | 310 | 15/42 | 100/4 | |
| | 1:2 | | | 474 | 6/4 | 45/24 | 155(37), 165(100) |
| Hyl | 1:2 | | 254–255d | 490 | 12/10 | 100/68 | 155(74), 156(49), 173(6), 183(11), 121(3), 107(2) |
| Asn | 1:1 | | 225–226 | 296 | 42/20 | 100/38 | 61(48) |
| Trp | 1:1 | 0.08 | 249–250 | 368 | 100/88 | 43/36 | |
| | 1:2 | | | 532 | 0.4/0.2 | —/— | 238(100) |
| His | 1:1 | 33.3 | 277–278d | 319 | 2/4 | 100/41 | 105(29) |
| | 1:2 | | | 483 | 2/1 | 17/10 | 155(100), 156(61) |
| Arg | 1:1 | | 244–245 | 338 | 3/5 | 100/25 | 59(11), 60(17), 137(35), 136(31) |

[a]Values are not corrected for the $B^{11}/B^{10}$ isotope ratio.
[b]The mass spectra for amino acids not showing a m.p. were obtained on the reaction mixtures.

4. Reaction of Glutamine and DPBA:Ethanolamine Adduct 0.58 g of DPBA:ethanolamine adduct, 0.29 g glutamine, 0.16 g acetic acid, 2 ml ethanol, and 8 ml water were mixed together and heated on a hotplate to near boil for 10 minutes; the solution was then stoppered and let sit for 16 hours. The precipitate was filtered off and washed with cyclohexane and water to obtain the product.

5. Reaction of Lysine Monohydrochloride with NaB(Ph)$_4$ 0.37 g dl-lysine, 0.68 g NaB(Ph)$_4$, 0.2 ml concentrated hydrochloric acid, and 40 ml water were mixed together and refluxed for 16 hours. An oil deposited which could not be solidified. Benzene was added to the cold reaction mixture, and the resultant mixture partitioned. The aqueous phase was washed two times with benzene, and 0.68 g NaB(Ph)$_4$ was added to form the amine salt. The salt was washed several times with water and became gelatinous; it was then spun down and rewashed with water to give the product.

Mass Spectra Data and Analysis

FIG. 1 displays an example of a spectrum of an α-amino acid (proline):DPBA adduct. It exhibits all the losses typically observed for the boroxazolidone ring, i.e. (a) the elimination of a phenyl group [M-77]+ by radical loss from the parent ion, giving rise to an ion signal which is often the base peak, (b) a neutral benzene elimination [M-78]+·, (c) the loss of carbon monoxide [M-28]+ and carbon dioxide [M-44]+ from either [M]+· or [M-1]+ by ring contraction, and (d) a combination thereof [M-78-28]+ for the ion signal at m/z 173. Table 2. Though ion signals for the losses caused by ring contraction were consistently observed with intensities ranging from 2 to 25%, these peaks were not included in table 2. Losses from the side chain were readily interpretable. The abundant ion signals are due to combinations of side-chain losses, mostly β-eliminations and McLafferty-type rearrangements, and an additional loss from the boroxazolidone ring (table 3).

TABLE 3

| Losses from side chain | Side-chain and combined losses Boroxazolidone ring | | | | |
|---|---|---|---|---|---|
| | [M]+·/−1 | −28/29 | −44 | −77 | −78 |
| Ammonia | 17 | | | 61 | |
| Water | 18 | 18 | 47 | 62 | 95 | 96 |
| Hydrogen sulfide | 34 | 34 | | | |
| Isopropene | 42 | | | | 120 |
| Isobutyl | 57 | | 85 | | |
| Guanidino | 59/60 | 59/60 | | | 137 |
| Phenyl | 77 | | 105/106 | 121 | 155 |
| Benzyl | 92 | 92 | 119 | | |
| Hydroxyphenyl | 93 | | 121 | | |
| Diphenylboron | 165 | 165/66 | | | |
| O—diphenylborono | | | | | |
| Hydroxybenzyl | 271 | 271 | | | |
| N—Diphenylborono | | | | | |
| Methylindole | 294 | 294 | | | |

With amino acids containing polar functional groups in the side chain, ion signals for the 1:1 and 1:2 complexes were observed. The ion signals arising from the 1:2 complexes were, however, considerably less abundant than those for the 1:1 adducts. They were most abundant when the mass spectra were obtained on crude reaction mixtures directly. In these mass spectra, ion signals from the reagent and its anhydrides were often prominent (table 1).

HPLC Data of Amino Acid:DPBA Adducts

Thirteen amino acid:DPBA adducts prepared by the above methods were mixed together and passed through an HPLC column. FIG. 2 presents the results; the thirteen adducts separated from each other and from the major decomposition products of DPBA, phenol and phenyborinic acid, both of which eluted in front of glutamic acid. The quantity of each adduct present can be determined by calculating the area under the adduct's corresponding peak.

TLC Data for α-Amino Acid:DPBA Adducts

Table 4 presents tlc data for five amino acid:DPBA adducts. The adducts were detected using UV light and, in the alternative, ninhydrin spray.

TABLE 4

| TLC data for 5 α-amino acid:DPBA adducts | | |
|---|---|---|
| Amino Acid | Solvent System | $R_f$ |
| Glu | Methylene chloride: | 0.12 |
| Tyr | Methanol 90:10 | 0.62 |
| Thr | | 0.59 |
| Leu | | 0.90 |
| Phe | | 0.94 |
| Glu | Methylene chloride: | 0.16 |
| Tyr | Isopropanol 90:10 | 0.75 |
| Thr | | 0.70 |
| Leu | | 0.95 |
| Phe | | 1.0 |
| Glu | Methylene chloride: | 0.03 |
| Tyr | Isopropanol:Acetonitrile | 0.41 |
| Thr | 90:5:5 | 0.37 |
| Leu | | 0.75 |
| Phe | | 0.78 |

We claim:

1. A method of forming and analyzing analyzable adducts in a mixture of compounds, wherein the method comprises contacting a mixture containing one or more compounds containing the functionality

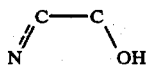

with a boron reagent such that the boron reagent reacts with said one or more compounds to form analyzable adducts, wherein —OH is either a hydroxy or the —OH portion of a carboxyl group, and N is part of an amino group, an imino group, or an aromatic heterocycle, and the boron reagent has the formula of either

where each X and Y is, independently, an alkyl group of 12 or fewer carbons or an aryl group of 6-20 carbons; or $BZ_3$, where each Z is, independently, an alkyl group of 12 or fewer carbons, or an aryl group of 6-20 carbons; and analyzing said analyzable adducts either by a chromatographic technique or by mass spectroscopy.

2. The method of claim 1, wherein said mixture is a protein hydrolysate.

3. The method of claim 1, wherein said mixture contains different α-amino acids.

4. The method of claim 1, wherein said mixture contains 2-carboxypyrazines.

5. The method of claim 1, wherein said reagent is 1,1-diphenylborinic acid.

6. The method of claim 1, wherein said mixture contains different γ-glutamyl peptides or β-aspartyl peptides.

7. The method of claim 1, wherein said mixture contains a primary amine, and said method comprises, prior to said contacting said mixture with said boron reagent, contacting said mixture with either an α-ketoacid or glyoxylic acid, and NaCNBH$_4$, such that the α-ketoacid or glyoxylic acid reacts with the primary amine in the presence of the NaCNBH$_4$ to form an α-amino acid which contains said funtionality and in which the α-amine is a secondary amine.

8. The method of claim 1, wherein said analyzable adducts are analyzed by a chromatographic technique.

9. The method of claim 1, wherein said analyzable adducts are analyzed by mass spectroscopy.

10. The method of claim 9, wherein said analysis by mass spectroscopy comprises comparing the mass spectra of said adducts to the mass spectra of controls.

11. The method of claim 1, wherein said analyzable adducts are analyzed by a chromatographic technique, wherein said chromatographic technique is high performance liquid chromatography.

12. The method of claim 1, wherein said analyzable adducts are analyzed by a said chromatographic technique, wherein said chromatographic technique is thin layer chromatography.

13. The method of claims 11 or 12, wherein during said analyzing step said adducts are detected by UV absorption.

14. The method of claim 12, wherein said analysis by thin layer chromatography comprises comparing the $R_f$'s of said adducts to the $R_f$'s of controls.

15. The method of claim 11, wherein said analysis by high performance liquid chromatography comprises determining the retention times of said adducts and comparing said retention times to the retention times of controls.

16. The method of claim 15, comprising the additional step of determining the quantity of each said adduct formed.

17. The method of claim 1, wherein said reagent is triphenylboron.

18. The method of claim 17, wherein said triphenylboron is generated in situ.

19. The method of claim 18, wherein said in situ generation is from sodium tetraphenylboron.

20. The method of claim 1, wherein said mixture contains a primary or secondary amine or a primary or secondary alcohol, and said method comprises, prior to said contacting said mixture with said boron reagent, contacting said mixture with a compound having the functionality of either

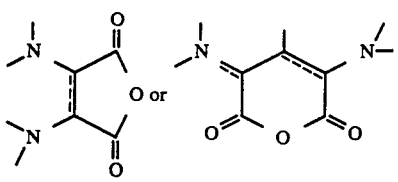

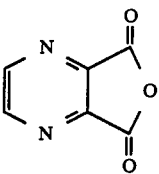

where N is part of an amino group, an imino group, or an aromatic heterocycle, such that the compound which contacts said mixture reacts with the primary or secondary amine or the primary or secondary alcohol to form a compound containing the functionality

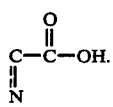

21. The method of claim 20, wherein said compound which contacts said mixture has the structure

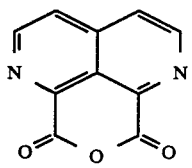

22. The method of claim 20, wherein said mixture contains a steroidal alcohol.

23. The method of claim 20, wherein said compound which contacts said mixture is an aromatic heterocycle.

24. The method of claim 23, wherein said compound which contacts said mixture has the structure 25. The method of claim 1, wherein said mixture contains a ketone or aldehyde, and said method comprises, prior to said contacting said mixture with said boron reagent, contacting said mixture with a compound that, in addition to having said functionality, also contains a hydrazide group, such that the compound which contacts said mixture reacts with the ketone or aldehyde to form a compound that contains both said functionality and

where $C^1$ is the carbonyl carbon of said ketone or aldehyde.

26. The method of claim 25, wherein said compound that contacts said mixture is a nitrogen-containing aromatic heterocycle.

27. The method of claim 26, wherein said compound that contacts said mixture has the structure

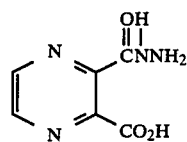

28. The method of claim 25, wherein said compound that contacts said mixture is a hydrazide containing α-amino acid.

29. The method of claim 28, wherein said amino acid is either γ-glutamyl hydrazide or β-aspartyl hydrazide.

* * * * *